United States Patent [19]
Staunton et al.

[11] Patent Number: 5,693,483
[45] Date of Patent: Dec. 2, 1997

[54] CYTOPLASMIC MODULATORS OF INTEGRIN BINDING/SIGNALLING

[75] Inventors: Donald E. Staunton, Kirkland; Edith Salot Harris, Seattle, both of Wash.

[73] Assignee: ICOS Corporation, Bothell, Wash.

[21] Appl. No.: 583,318

[22] Filed: Jan. 5, 1996

[51] Int. Cl.$^6$ .................. C12Q 1/02; C12Q 1/37; A61K 38/00; G01N 33/53
[52] U.S. Cl. .................. 435/29; 435/23; 435/24; 435/7.1; 435/4; 530/388.26; 530/300; 530/350
[58] Field of Search .................. 435/29, 23, 24, 435/7.1, 4; 530/388.26, 300, 350

[56] References Cited

U.S. PATENT DOCUMENTS

| | | | |
|---|---|---|---|
| 5,149,780 | 9/1992 | Plow et al. | 530/324 |
| 5,366,862 | 11/1994 | Venton et al. | 435/23 |

OTHER PUBLICATIONS

Anwar et al., "Adhesion to Fibronectin Prolongs Eosinophil Survival," *J. Exp. Med.*, 177:839–843 (1993) month not available.

Arnaout, Amin M., "Structure and Function of the Leukocyte Adhesion Molecules CD11/CD18," *Blood* 75(5):1037–1050 (1990) month not available.

Baeuerle and Henkel, "Function and Activation of NK–κB in the Immune System," *Annu. Rev. Immunol.*, 12:141–179 (1994) month not available.

Baron et al. "The Pathogenesis of Adoptive Murine Autoimmune Diabetes Requires an Interaction between α4–Integrins and Vascular Cell Adhesion Molecule-1," *J. Clin. Invest.* 93:1700–1708 (1994) month not available.

Baron et al. "Surface Expression of α4 Integrin by CD4 T Cells Is Required for Their Entry into Brain Parenchyma," *J. Exp. Med.* 177:57–68 (1993) month not available.

Boldin et al. "A Protein Related to a Proteasomal Subunit Binds to the Intracellular Domain of the p55 TNF Receptor Upstream to its 'Death Domain'," *FEBS Letters* 367:39–44 (1995) month not available.

Burkly et al., "Protection Against Adoptive Transfer of Autoimmune Diabetes Mediated Through Very Late Antigen–4 Integrin," *Diabetes* 43:529–534 (1994) month not available.

Clark and Brugge, "Integrins and Signal Transduction Pathways" The Road Taken, *Science* 268:233–239 (1995) month not available.

Durfee et al., "The Retinoblastoma Protein Associates with the Protein Phosphatase Type 1 Catalytic Subunit," *Genes & Development* 7:555–569 ((1993) month not available.

Ferguson et al., "Antigen–Independent Processes in Antigen–Specific Immunity," *J. Immunol.* 150(4):1172–1182 (1993) month not available.

Flores–Romo et al., "Anti–CD40 Antibody Stimulates the VLA–4–dependent Adhesion of Normal and LFA–1–deficient B Cells to Endothelium," *Immunol.*, 79:445–451 (1993) month not avialable.

Goldberg, A.L., "Functions of the Proteasome: The Lysis at the End of the Tunnel," *Science*, 268;522–523 (1995) month not available.

Gumbiner et al., "Proteins Associated with the Cytoplasmic Surface of Adhesion Molecules," *Neuron* 11:551–564 (1993) month not available.

Hemler et al., "Structure of the Integrin VLA–4 and its Cell–Cell and Cell–Matrix Adhesion Functions," *Immunol Rev.* 114:45–60 (1990) month not available.

Kilshaw et al. "A New Surface Antigen on Intraepithelial Lymphocytes in the Intestine," *Eur. J. Immunol.* 20:2201–2207 (1990) month not available.

Kishimoto et al., "Cloning of the β Subunit of the Leukocyte Adhesion Proteins: Homology to an Extracellular Matrix Receptor Defines a Novel Supergene Family," *Cell* 48:681–690 (1987) month not available.

LaFlamme et al., "Regulation of Fibronectin Receptor Distribution," *J. Cell Biol.* 117(2):437–447 (1992) month not available.

Lazarovits and Karsh, "Differential Expression in Rheumatoid Synovium and Synovial Fluid of α4β7 Integrin," *J. Immunol.* 151(11):6482–6489 (1993) month not available.

Lobb and Hemler, "The Pathophysiologic Role of α4 Integrins In Vivo," *J. Clin. Invest.* 94:1722–1728 (1994) month not available.

Lofquist et al., "Transcription–independent Turnover of IκBα during Nomocytes Adherence; Implications for a Translational Component etc/MAD–3 mRNA Levels, " *Mol. Cell. Biol.*, 15:1737–1746 (1995) month not available.

McEver, Rodger P., "Leukocyte–Endothelial Cell Interactions," *Curr. Opin. Cell. Biol.* 4:840–849 (1992) month not available.

Milne and Piper, "The Role of the VLA–4 Integrin in a Model of Airway Inflammation in the Guinea–Pig," *Br. J. Pharmacol* 112:82P (Abstr) (1994) month not available.

Miyamoto et al., "Synergistic Role for Receptor Occupancy and Aggregation in Integrin Transmembrane Function," *Science* 267:883–835 (1995) month not available.

Mulligan et al., "Role of $\alpha_1$, $\beta_2$ Integrins and ICAM–1 in Lung Injury after Deposition of IgG and IgA Immune Complexes," *J. Immunol.* 150(6):2407–2417 (1993a) month not available.

Mulligan et al., "Requirements for Leukocyte Adhesion Molecules in Nephrotoxic Nephritis," *J. Clin. Invest.* 91:577–587 (1993b) month not available.

(List continued on next page.)

*Primary Examiner*—Louise Leary
*Attorney, Agent, or Firm*—Marshall, O'Toole, Gerstein, Murray & Borun

[57] ABSTRACT

The present invention relates to methods to identify modulators of integrin binding and/or signalling activity. Specifically the invention relates to a method to identify compounds which can alter the interaction between the cytoplasmic domain of a $\beta_1$ integrin and a proteasome subunit protein.

1 Claim, No Drawings

OTHER PUBLICATIONS

Nakajima et al., "Role of Vascular Cell Adhesion Molecule 1/Very Late Activation Antigen 4 and Intercellular Adhesion Molecule 1/Lymphocyte Function–associated Antigen 1 Interactions in Antigen–induced Eosinophil and T Cell Recruitment into the Tissue," *J. Exp. Med.* 179:1245–1154 (1994) month not available.

Paul et al., "The Efficacy of LFA–1 and VLA–4 Antibody Treatment in Rat Vascularized Cardiac Allograft Rejection," *Transplantation*, 55(5):1196–1199 (1993) month not available.

Pavalko and Otey, "Role of Adhesion Molecule Cytoplasmic Domains in Mediating Interactions with the Cytoskeleton," *Proc. Soc. Exp. Biol. Med.*, 205:282–293, 1994 month not available.

Podolsky et al., "Attenuation of Colitis in the Cotton–top Tamarin by Anti–$\alpha$4 integrin Monoclonal Antibody," *J. Clin. Invest.* 92:372–380 (1993) month not available.

Pretolani et al., "Antibody to Very Late Activation Antigen 4 Prevents Antigen–induced Bronchial Hyperactivity and Cellular Infiltration in the Guinea Pig Airways," *J. Exp. Med.* 180:795–805 (1994) month not available.

Schweighoffer et al., "Selective Expression of Integrin $\alpha 4\beta 7$ on a Subset of Human CD4$^+$Memory T Cells with hallmarks of Gut–Trophism," *J. Immunol.* 151(2):717–729 (1993) month not available.

Sharma et al., "Direct Interaction of Filamin (ABP–280) with the $\beta$2–Integrin Subunit CD18," *J. Immunol.* 154:3461–3470 (1995) month not available.

Siebenlist et al., "Structure, Regulation and Function of NF–$\kappa$B" *Annu. Rev. Cell Biol.*, 10:405–455 (1994) month not available.

Song et al., "Identification of a Protein with Homology to hsp90 That Binds the Type 1 Tumor Necrosis Factor Receptor*," vol. 270, No. 8:3574–3581 (1995) month not available.

Springer et al., "Traffic Signals for Lymphocyte Recirculation and Leukocyte Emigration: The Multistep Paradigm," *Cell* 76:301–314 (1994) month not available.

Tsurumi et al., "cDNA Cloning and Functional Analysis of the p97 Subunit of the 26S Proteasome, a Polypeptide Identical to the Type–1 Tumor–Necrosis–Factor–Receptor–Associated Protein–2/55.11," *Eur. J. Biochem:*239, 912–921 (1996) month not available.

Van der Vireen et al., "A Novel Leukointegin, $\alpha d\beta 2$, Binds Preferentially to ICAM–3," *Immunity* 3:683–690 (1995) month not available.

Weg et al., "A Monoclonal Antibody Recognizing Very Late Activation Antigen–4 Inhibits Eosinophil Accumulation In Vivo," *J. Exp. Med.* 177:561–566 (1993) month not available.

Winn and Harlan, "CD18–Independent Neutrophil and Mononuclear Leukocyte Emigration into the Peritoneum of Rabbits," *J. Clin. Invest.* 92:1168–1173 (1993) month not available.

Yang et al., "Inhibition of Insulitis and Prevention of Diabetes in Nonobese Diabetic Mice by Blocking L–selectin and Very Late Antigen 4 Adhesion Receptors," *Proc. Natl. Acad. Sci. USA* 90:10494–10498 (1993) month not available.

Yednock et al., "Precention of Experimental Autoimmune Encephalomyelits by Antibodies Against $\alpha 4\beta 1$ Integrin," *Nature* 356:63–66 (1992) month not available.

Yurochko et al., "Integrins as a Primary Signal Transduction Molecule Regulating Monocyte Immediate–early Gene Induction," *Proc. Natl. Acad. Sci. (USA)*, 89:9034–9038 (1992) month not avialable.

Wizel et al; "Europ. J. Immunol."; vol. 24, pp. 1487–1495, 1994 month not available.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:1:

AGAAGTAGGT ATTCCTTCCT G      21

( 2 ) INFORMATION FOR SEQ ID NO:2:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

GGAAGATCTT GAAGCTTTTA ATGATAATTC                30

( 2 ) INFORMATION FOR SEQ ID NO:3:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:3:

GGAAGATCTT CATTTTCCT CATACTTCGG                 30

( 2 ) INFORMATION FOR SEQ ID NO:4:

( i ) SEQUENCE CHARACTERISTICS:
  ( A ) LENGTH: 1631 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 1..1437

( x i ) SEQUENCE DESCRIPTION: SEQ ID NO:4:

| GAC | AAG | TAC | CTG | TAC | TCC | TCT | GAG | GAC | TAC | ATT | AAG | TCA | GGA | GCT | CTT | 48 |
| Asp | Lys | Tyr | Leu | Tyr | Ser | Ser | Glu | Asp | Tyr | Ile | Lys | Ser | Gly | Ala | Leu | |
| 1 | | | | 5 | | | | | 10 | | | | | 15 | | |

| CTT | GCC | TGT | GGC | ATA | GTG | AAC | TCT | GGG | GTC | CGG | AAT | GAG | TGT | GAC | CCT | 96 |
| Leu | Ala | Cys | Gly | Ile | Val | Asn | Ser | Gly | Val | Arg | Asn | Glu | Cys | Asp | Pro | |
| | | | 20 | | | | | 25 | | | | | 30 | | | |

| GCT | CTG | GCA | CTG | CTC | TCA | GAC | TAT | GTT | CTC | CAC | AAC | AGC | AAC | ACC | ATG | 144 |
| Ala | Leu | Ala | Leu | Leu | Ser | Asp | Tyr | Val | Leu | His | Asn | Ser | Asn | Thr | Met | |
| | | 35 | | | | | 40 | | | | | 45 | | | | |

| AGA | CTT | GGT | TCC | ATC | TTT | GGG | CTA | GGC | TTG | GCT | TAT | GCT | GGC | TCA | AAT | 192 |
| Arg | Leu | Gly | Ser | Ile | Phe | Gly | Leu | Gly | Leu | Ala | Tyr | Ala | Gly | Ser | Asn | |
| | 50 | | | | | 55 | | | | | 60 | | | | | |

| CGT | GAA | GAT | GTC | CTA | ACA | CTG | CTG | CTG | CCT | GTG | ATG | GGA | GAT | TCA | AAG | 240 |
| Arg | Glu | Asp | Val | Leu | Thr | Leu | Leu | Leu | Pro | Val | Met | Gly | Asp | Ser | Lys | |
| 65 | | | | | 70 | | | | | 75 | | | | | 80 | |

| TCC | AGC | ATG | GAG | GTG | GCA | GGT | GTC | ACA | GCT | TTA | GCC | TGT | GGA | ATG | ATA | 288 |
| Ser | Ser | Met | Glu | Val | Ala | Gly | Val | Thr | Ala | Leu | Ala | Cys | Gly | Met | Ile | |
| | | | | 85 | | | | | 90 | | | | | 95 | | |

| GCA | GTA | GGG | TCC | TGC | AAT | GGA | GAT | GTA | ACT | TCC | ACT | ATC | CTT | CAG | ACC | 336 |
| Ala | Val | Gly | Ser | Cys | Asn | Gly | Asp | Val | Thr | Ser | Thr | Ile | Leu | Gln | Thr | |
| | | | 100 | | | | | 105 | | | | | 110 | | | |

| ATC | ATG | GAG | AAG | TCA | GAG | ACT | GAG | CTC | AAG | GAT | ACT | TAT | GCT | CGT | TGG | 384 |
| Ile | Met | Glu | Lys | Ser | Glu | Thr | Glu | Leu | Lys | Asp | Thr | Tyr | Ala | Arg | Trp | |
| | | 115 | | | | | 120 | | | | | 125 | | | | |

| CTT | CCT | CTT | GGA | CTG | GGT | CTC | AAC | CAC | CTG | GGG | AAG | GGT | GAG | GCC | ATC | 432 |
| Leu | Pro | Leu | Gly | Leu | Gly | Leu | Asn | His | Leu | Gly | Lys | Gly | Glu | Ala | Ile | |
| | 130 | | | | | 135 | | | | | 140 | | | | | |

| GAG | GCA | ATC | CTG | GCT | GCA | CTG | GAG | GTT | GTG | TCA | GAG | CCA | TTC | CGC | AGT | 480 |
| Glu | Ala | Ile | Leu | Ala | Ala | Leu | Glu | Val | Val | Ser | Glu | Pro | Phe | Arg | Ser | |
| 145 | | | | | 150 | | | | | 155 | | | | | 160 | |

| TTT | GCC | AAC | ACA | CTG | GTG | GAT | GTG | TGT | GCA | TAT | GCA | GGC | TCT | GGG | AAT | 528 |

-continued

|     |     |     |     | Phe | Ala | Asn | Thr | Leu | Val | Asp | Val | Cys | Ala | Tyr | Ala | Gly | Ser | Gly | Asn |      |
|-----|-----|-----|-----|-----|-----|-----|-----|-----|-----|-----|-----|-----|-----|-----|-----|-----|-----|-----|-----|------|
|     |     |     |     |     |     |     |     | 165 |     |     |     | 170 |     |     |     |     |     | 175 |     |      |

```
GTG CTG AAG GTG CAG CAG CTG CTC CAC ATT TGT AGC GAA CAC TTT GAC              576
Val Leu Lys Val Gln Gln Leu Leu His Ile Cys Ser Glu His Phe Asp
            180                 185                 190

TCC AAA GAG AAG GAG GAA GAC AAA GAC AAG AAG GAA AAG AAA GAC AAG              624
Ser Lys Glu Lys Glu Glu Asp Lys Asp Lys Lys Glu Lys Lys Asp Lys
        195                 200                 205

GAC AAG AAG GAA GCC CCT GCT GAC ATG GGA GCA CAT CAG GGA GTG GCT              672
Asp Lys Lys Glu Ala Pro Ala Asp Met Gly Ala His Gln Gly Val Ala
    210                 215                 220

GTT CTG GGG ATT GCC CTT ATT GCT ATG GGG GAG GAG ATT GGT GCA GAG              720
Val Leu Gly Ile Ala Leu Ile Ala Met Gly Glu Glu Ile Gly Ala Glu
225                 230                 235                 240

ATG GCA TTA CGA ACC TTT GGC CAC TTG CTG AGA TAT GGG GAG CCT ACA              768
Met Ala Leu Arg Thr Phe Gly His Leu Leu Arg Tyr Gly Glu Pro Thr
                245                 250                 255

CTC CGG AGG GCT GTA CCT TTA GCA CTG GCC CTC ATC TCT GTT TCA AAT              816
Leu Arg Arg Ala Val Pro Leu Ala Leu Ala Leu Ile Ser Val Ser Asn
            260                 265                 270

CCA CGA CTC AAC ATC CTG GAT ACC CTA AGC AAA TTC TCT CAT GAT GCT              864
Pro Arg Leu Asn Ile Leu Asp Thr Leu Ser Lys Phe Ser His Asp Ala
        275                 280                 285

GAT CCA GAA GTT TCC TAT AAC TCC ATT TTT GCC ATG GGC ATG GTG GGC              912
Asp Pro Glu Val Ser Tyr Asn Ser Ile Phe Ala Met Gly Met Val Gly
    290                 295                 300

AGT GGT ACC AAT AAT GCC CGT CTG GCT GCA ATG CTG CGC CAG TTA GCT              960
Ser Gly Thr Asn Asn Ala Arg Leu Ala Ala Met Leu Arg Gln Leu Ala
305                 310                 315                 320

CAA TAT CAT GCC AAG GAC CCA AAC AAC CTC TTC ATG GTG CGC TTG GCA             1008
Gln Tyr His Ala Lys Asp Pro Asn Asn Leu Phe Met Val Arg Leu Ala
                325                 330                 335

CAG GGC CTG ACA CAT TTA GGG AAG GGC ACC CTT ACC CTC TGC CCC TAC             1056
Gln Gly Leu Thr His Leu Gly Lys Gly Thr Leu Thr Leu Cys Pro Tyr
            340                 345                 350

CAC AGC GAC CGG CAG CTT ATG AGC CAG GTG GCC GTG GCT GGA CTG CTC             1104
His Ser Asp Arg Gln Leu Met Ser Gln Val Ala Val Ala Gly Leu Leu
        355                 360                 365

ACT GTG CTT GTC TCT TTC CTG GAT GTT CGA AAC ATT ATT CTA GGC AAA             1152
Thr Val Leu Val Ser Phe Leu Asp Val Arg Asn Ile Ile Leu Gly Lys
    370                 375                 380

TCA CAC TAT GTA TTG TAT GGG CTG GTG GCT GCC ATG CAG CCC CGA ATG             1200
Ser His Tyr Val Leu Tyr Gly Leu Val Ala Ala Met Gln Pro Arg Met
385                 390                 395                 400

CTG GTT ACG TTT GAT GAG GAG CTG CGG CCA TTG CCA GTG TCT GTC CGT             1248
Leu Val Thr Phe Asp Glu Glu Leu Arg Pro Leu Pro Val Ser Val Arg
                405                 410                 415

GTG GGC CAG GCA GTG GAT GTG GTG GGC CAG GCT GGC AAG CCG AAG ACT             1296
Val Gly Gln Ala Val Asp Val Val Gly Gln Ala Gly Lys Pro Lys Thr
            420                 425                 430

ATC ACA GGG TTC CAG ACG CAT ACA ACC CCA GTG TTG TTG GCC CAC GGG             1344
Ile Thr Gly Phe Gln Thr His Thr Thr Pro Val Leu Leu Ala His Gly
        435                 440                 445

GAA CGG GCA GAA TTG GCC ACT GAG GAG TTT CTT CCT GTT ACC CCC ATT             1392
Glu Arg Ala Glu Leu Ala Thr Glu Glu Phe Leu Pro Val Thr Pro Ile
    450                 455                 460

CTG GAA GGT TTT GTT ATC CTT CGG AAG AAC CCC AAT TAT GAT CTC                 1437
Leu Glu Gly Phe Val Ile Leu Arg Lys Asn Pro Asn Tyr Asp Leu
465                 470                 475

TAAGTGACCA CCAGGGGCTC TGAACTGTAG CTGATGTTAT CAGCAGGCCA TGCATCCTGC           1497
```

```
TGCCAAGGGT GGACACGGCT GCAGACTTCT GGGGGAATTG TCGCCTCCTG CTCTTTTGTT    1557

ACTGAGTGAG ATAAGGTTGT TCAATAAAGA CTTTTATCCC CAAAAAAAAA AAAAAAAAA     1617

AAAAAAAAAA AAAA                                                      1631
```

( 2 ) INFORMATION FOR SEQ ID NO:5:

( i ) SEQUENCE CHARACTERISTICS:
        ( A ) LENGTH: 479 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Asp Lys Tyr Leu Tyr Ser Ser Glu Asp Tyr Ile Lys Ser Gly Ala Leu
 1               5                  10                  15

Leu Ala Cys Gly Ile Val Asn Ser Gly Val Arg Asn Glu Cys Asp Pro
                20                  25                  30

Ala Leu Ala Leu Leu Ser Asp Tyr Val Leu His Asn Ser Asn Thr Met
            35                  40                  45

Arg Leu Gly Ser Ile Phe Gly Leu Gly Leu Ala Tyr Ala Gly Ser Asn
 50                  55                  60

Arg Glu Asp Val Leu Thr Leu Leu Leu Pro Val Met Gly Asp Ser Lys
 65                  70                  75                  80

Ser Ser Met Glu Val Ala Gly Val Thr Ala Leu Ala Cys Gly Met Ile
                85                  90                  95

Ala Val Gly Ser Cys Asn Gly Asp Val Thr Ser Thr Ile Leu Gln Thr
                100                 105                 110

Ile Met Glu Lys Ser Glu Thr Glu Leu Lys Asp Thr Tyr Ala Arg Trp
            115                 120                 125

Leu Pro Leu Gly Leu Gly Leu Asn His Leu Gly Lys Gly Glu Ala Ile
130                 135                 140

Glu Ala Ile Leu Ala Ala Leu Glu Val Val Ser Glu Pro Phe Arg Ser
145                 150                 155                 160

Phe Ala Asn Thr Leu Val Asp Val Cys Ala Tyr Ala Gly Ser Gly Asn
                165                 170                 175

Val Leu Lys Val Gln Gln Leu Leu His Ile Cys Ser Glu His Phe Asp
                180                 185                 190

Ser Lys Glu Lys Glu Glu Asp Lys Asp Lys Lys Glu Lys Lys Asp Lys
            195                 200                 205

Asp Lys Lys Glu Ala Pro Ala Asp Met Gly Ala His Gln Gly Val Ala
210                 215                 220

Val Leu Gly Ile Ala Leu Ile Ala Met Gly Glu Glu Ile Gly Ala Glu
225                 230                 235                 240

Met Ala Leu Arg Thr Phe Gly His Leu Leu Arg Tyr Gly Glu Pro Thr
                245                 250                 255

Leu Arg Arg Ala Val Pro Leu Ala Leu Ala Leu Ile Ser Val Ser Asn
                260                 265                 270

Pro Arg Leu Asn Ile Leu Asp Thr Leu Ser Lys Phe Ser His Asp Ala
            275                 280                 285

Asp Pro Glu Val Ser Tyr Asn Ser Ile Phe Ala Met Gly Met Val Gly
290                 295                 300

Ser Gly Thr Asn Asn Ala Arg Leu Ala Ala Met Leu Arg Gln Leu Ala
305                 310                 315                 320

Gln Tyr His Ala Lys Asp Pro Asn Asn Leu Phe Met Val Arg Leu Ala
```

|     |     |     |     |     | 325 |     |     |     |     | 330 |     |     |     |     | 335 |     |     |
|-----|-----|-----|-----|-----|-----|-----|-----|-----|-----|-----|-----|-----|-----|-----|-----|-----|-----|

Gln Gly Leu Thr His Leu Gly Lys Gly Thr Leu Thr Leu Cys Pro Tyr
                340                     345                 350

His Ser Asp Arg Gln Leu Met Ser Gln Val Ala Val Ala Gly Leu Leu
            355                 360                 365

Thr Val Leu Val Ser Phe Leu Asp Val Arg Asn Ile Ile Leu Gly Lys
    370                 375                 380

Ser His Tyr Val Leu Tyr Gly Leu Val Ala Ala Met Gln Pro Arg Met
385                     390                 395                 400

Leu Val Thr Phe Asp Glu Leu Arg Pro Leu Pro Val Ser Val Arg
                405             410             415

Val Gly Gln Ala Val Asp Val Val Gly Gln Ala Gly Lys Pro Lys Thr
            420                 425                 430

Ile Thr Gly Phe Gln Thr His Thr Thr Pro Val Leu Leu Ala His Gly
        435                 440                 445

Glu Arg Ala Glu Leu Ala Thr Glu Glu Phe Leu Pro Val Thr Pro Ile
    450                 455                 460

Leu Glu Gly Phe Val Ile Leu Arg Lys Asn Pro Asn Tyr Asp Leu
465                 470                 475

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TACGGCACTC TTATACTAAG GATTTTCACC CGT      33

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

ATTGACCAGA GTTGTCTAGG CACTCTTATA AAT      33

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TCATTTTCCC TCATACTACG GATTGACCAC AGT      33

( 2 ) INFORMATION FOR SEQ ID NO:9:

( i ) SEQUENCE CHARACTERISTICS:
        ( A ) LENGTH: 33 base pairs
        ( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:9:

GTCCCATTTG GCATTCTATT TCTCCTTTTC AAA    33

( 2 ) INFORMATION FOR SEQ ID NO:10:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Lys Leu Leu Met Ile Ile His Asp Arg Arg Glu Phe Ala Lys Phe Glu
1               5                   10                  15

Lys Glu Lys Met Asn Ala Lys Trp Asp Thr Gly Glu Asn Pro Ile Tyr
                20                  25                  30

Lys Ser Ala Val Thr Thr Val Val Asn Pro Lys Tyr Glu Gly Lys
            35                  40                  45
```

( 2 ) INFORMATION FOR SEQ ID NO:11:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Lys Leu Met Ile Ile His Asp Arg Arg Glu Phe Ala Lys Phe Glu Lys
1               5                   10                  15

Glu Lys Met Asn Ala Lys Trp Asp Thr Gly Glu Asn Pro
                20                  25
```

( 2 ) INFORMATION FOR SEQ ID NO:12:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Lys Leu Leu Met Ile Ile His Asp Arg Arg Glu Phe Ala Lys Phe Glu
1               5                   10                  15

Lys Glu Lys Met Asn Ala Lys Trp Asp Thr Gly Glu Asn Pro Ile Tyr
                20                  25                  30

Lys Ser Ala
            35
```

( 2 ) INFORMATION FOR SEQ ID NO:13:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Lys Leu Leu Met Ile Ile His Asp Arg Arg Glu Phe Ala Lys Phe Glu
1               5                   10                  15

Lys Glu Lys Met Asn Ala Lys Trp Asp Thr Gly Glu Asn Pro Ile Tyr
            20              25                  30

Lys Ser Ala Val Thr Thr Val Val Asn Pro
        35              40

( 2 ) INFORMATION FOR SEQ ID NO:14:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

Lys Leu Leu Met Ile Ile His Asp Arg Arg Glu Phe Ala Lys Phe Glu
1               5                   10                  15

Lys Glu Lys

CYTOPLASMIC MODULATORS OF INTEGRIN BINDING/SIGNALLING

BACKGROUND

A significant characteristic of the immune and inflammatory responses is the movement of leukocytes from the bloodstream into specific tissues in response to various physiological signals. For example, certain subsets of lymphocytes "home" to various secondary lymphoid tissues such as lymph nodes or Peyer's patches, and eventually return to circulation. Other leukocytes such as granulocytes and monocytes, however, do not return to circulation after transmigration from the bloodstream. Movement of leukocytes from circulation is effected by a series of receptor/counter-receptor interactions which are coordinated by various specific membrane adhesion molecules.

Extravasation of leukocytes from the bloodstream [for review, see McEver, *Curr. Opin. Cell Biol.* 4:840–849 (1992)] is initially effected by a family of membrane glycoproteins termed selectins which are either expressed constitutively or induced in response to specific cytokines. Binding of selectins to their counterpart ligand brings leukocytes into close, but not static, contact with vascular endothelial cells. The "tethered" leukocyte then begins a "rolling" process along the endothelium which continues until additional molecular interactions firmly stabilize a specific cell/cell interaction. One of the molecular binding activities which results in the stable interaction is effected by a second family of surface glycoproteins called integrins which possess a higher binding affinity for their respective ligands than selectins.

The integrins are heterodimeric surface molecules comprised of an $\alpha$ and a $\beta$ subunit in non-covalent association. All integrins are transmembrane proteins with counter-receptor binding activity localized in the extracellular domain. Integrins also possess relatively short cytoplasmic regions which participate in transmembrane signaling events. Integrins are capable of interacting with other cell-bound counter-receptors and components of the extracellular matrix, as well as soluble factors. Binding of extracellular ligands leads to crosslinking and localized clustering of integrins [Miyamoto, et al., *Science* 267:833, 1995] and formation of focal adhesions wherein the clustered integrin cytoplasmic domains associate with cytoskeletal components including, for example, actin filaments [Pavalko and Otey, *Proc. Soc. Exp. Biol. Med.* 205:32767, 1994, and Gumbiner, *Neuron* 11:551, 1993]. While most investigations into integrin physiological activity have focused on identifying specific counter-receptors using immunological methodologies as discussed infra, less is known about the specific interactions of integrins with cytoplasmic components. Mutation studies, however, have indicated that the cytoplasmic sequences are required for integrin association with focal contacts [LaFlamme, et al., *J. Cell. Biol.* 117:437 (1992)]. Other data discussed infra support this observation.

While numerous integrins have been identified, certain subsets are unique to leukocytes, with each member of the subset having characteristic cell-specific expression and counter-receptor binding properties. Of leukocyte-specific integrins, at least three $\beta_2$ integrins are known, each comprised of a unique $\alpha$ subunit in association with a $\beta_2$ subunit (designated CD18) [Kishimoto, et al., *Cell* 48:681–690 (1987)]. For a recent review of the state of the art with regard to $\beta_2$ integrins, see Springer, *Cell* 76:301–314 (1994). CD11a/CD18, also known as $\alpha_L\beta_2$ or LFA-1, is expressed on all leukocytes and has been shown to bind to ICAM-1, ICAM-2, and ICAM-3. CD11b/CD18, also know as $\alpha_M\beta_2$ or Mac-1, is expressed on polymorphonuclear neutrophils, monocytes and eosinophils and has been shown to bind to ICAM-1, complement factor iC3b, factor X, and fibrinogen. CD11c/CD18, also known as $\alpha_X\beta_2$ or p150,95, is expressed on monocytes, polymorphonuclear neutrophils and eosinophils and has been shown to bind to complement factor iC3b and fibrinogen. In addition, a fourth human $\beta_2$ integrin, designated $\alpha_d\beta_2$, has recently been identified [Van der Vieren, et al., *Immunity* 3:683–690 (1995)]. Recently, it has been demonstrated that the actin-binding protein, filamin, directly binds to a cytoplasmic portion of $\beta_2$ subunits [Sharma, et al., *J. Immunol.* 154:3461–3470 (1995)] which suggests a role one or more of for the $\beta_2$ integrins in formation of focal contacts and cell motility in general [see review in Arnaout, *Blood* 75:1037 (1990)].

A second subset of leukocyte specific integrins may be referred to as the $\alpha_4$ integrins in view of the fact that both members of the family are comprised of a common $\alpha_4$ subunit in association with either a $\beta_1$ or $\beta_7$ subunit. For a recent review, see Springer, supra. VLA-4, also referred to as $\alpha_4\beta_1$ or CD49d/CD29, is expressed on most peripheral blood leukocytes except neutrophils and specifically binds VCAM-1 and fibronectin. LPAM-1, also known as $\alpha_4\beta_7$, is expressed on all peripheral blood leukocytes and has been shown to bind MadCAM-1, fibronectin and VCAM-1. Expression of either of the $\alpha_4$ integrins has also been demonstrated in a wide range of leukocyte cell types in lymphoid organs and in various tissues (Hemler et al., *Immunol. Rev.* 114:45–60, 1990; Kilshaw et al., *Eur. J. Immunol.* 20:2201–2207, 1990; Schweighoffer et al., *J. Immunol.* 151:717–729, 1993; and Lazarovits and Karsh, *J. Immunol.* 151:6482–6489, 1993). Consistent with the observed participation of $\beta_2$ integrins in formation of focal contacts, presumably through filamin binding, it has previously been shown that cytoplasmic portions of $\beta_1$ integrins directly bind $\alpha$-actinin in vitro. While this interaction has not been demonstrated in vivo, it suggests physiological involvement of $\beta_1$ integrins in cell mobility and/or maintenance of cell morphology [see review in Clark and Brugge, *Science* 268:233–238 (1995)].

A number of in vitro and in vivo studies utilizing anti-$\alpha_4$ monoclonal antibodies have indicated a role for the $\alpha_4$ integrin pathophysiological conditions [see review, Lobb and Hemler, *J. Clin. Invest.* 94:1722–1728 (1994)]. For example, several investigations have provided evidence that $\alpha_4$ integrins are involved in leukocyte emigration from peripheral blood into regions of inflammation (Weg, et al., *J. Exp. Med.* 177:561–566, 1992; Winn and Harlan, *J. Clin. Invest.* 92:1168–1173, 1993). These observations suggest that anti-$\alpha_4$ antibodies may be capable of ameliorating integrin-associated disease states, and this therapeutic potential has been demonstrated in several animal disease state models. For example, bolus injection of antibodies to $\alpha_4$ integrins delayed the onset of paralysis in rat and murine experimental allergic encephalomyelitis (Yednock, et al., *Nature* 356:63–66, 1992; Baron, et al., *J. Exp. Med.* 177:57–68, 1993). Prophylactic administration of anti-$\alpha_4$ antibodies reduced ear swelling in murine contact hypersensitivity models (Ferguson, et al., *J. Immunol.* 150:1172–1182, 1993; Nakajima, et al., *J. Exp. Med.* 179:1145–1154, 1994). Further, anti-$\alpha_4$ antibodies were shown to reduce infiltration of pancreatic islets and delay the onset of diabetes in non-obese diabetic mice which are prone to spontaneous development of type I diabetes (Yang, et al., *Proc. Natl. Acad. Sci. (USA)* 90:10494–10498, 1993; Burkly, et al., *Diabetes* 43:529–534, 1994; Baron, et al., *J.*

*Clin. Invest.* 93:1700–1708, 1994). Still other in vivo studies using anti-$\alpha_4$ antibodies suggest a role for $\alpha_4$ integrins in allergic lung inflammation (Pretolani, et al., *J. Exp. Med.* 180:795–805 (1994); Milne and Piper, *Br. J. Pharmacol.* 112:82Pa(Abstr), 1994); inflammatory bowel disease (Podolsky, et al., *J. Clin. Invest.* 92:372–380, 1993); cardiac allograft rejection (Paul, et al., *Transplantation* 55:1196–1199, 1993); acute nephrotoxic nephritis (Mulligan, et al., *J. Clin. Invest.* 91:577–587, 1993); and immune complex mediated lung injury (Mulligan, et al., *J. Immunol.* 159:2407–2417, 1993).

Thus there exists a need in the art to identify molecules which bind to and/or modulate the binding and/or signalling activity of the integrins and to develop methods by which these molecules can be identified. The methods, and the molecules thereby identified, will provide practical means for therapeutic intervention in $\alpha_4$ integrin-mediated immune and inflammatory responses.

BRIEF DESCRIPTION OF THE INVENTION

The present invention provides methods wherein modulators (i.e., activators or inhibitors) of integrin-proteasome subunit interaction can be identified. A general method involves: i) contacting an integrin or fragment thereof with a proteasome subunit or fragment thereof; ii) measuring binding between the integrin or fragment thereof and the proteasome subunit or fragment thereof; iii) measuring binding between the integrin or fragment thereof and the proteasome subunit or fragment thereof in the presence of a test compound; and iv) comparing the measurement in step (ii) and the measurement in step (iii). A change in degree of interaction, either enhancement (indicating the compound is an activator) or abatement (indicating that the compound is an inhibitor), is indicative of the potential use of the modulator in an in vivo system to effect the same change.

Numerous variations on the general method are contemplated by the invention. For example, a two hybrid system may be utilized to identify genes encoding potential modulators. In this system, an integrin is expressed in a host cell as a fusion protein with either a DNA binding domain or transactivation domain of a modular transcription factor. A proteasome subunit protein is also expressed as a fusion protein with which ever transcription factor domain is not utilized with expression of the integrin fusion protein. Interaction of the two fusion proteins results in reconstitution of the holo-transcription factor and permits expression of a reporter gene with a promoter specific for the transcription factor. Use of this system in the presence or absence of library cDNA can permit identification of genes that encode proteins which modulate the degree of reporter gene expression.

As another example, either the integrin or the proteasome subunit can be immobilized on a solid support. The binding partner not immobilized can then be labeled in such a manner to permit detection of its binding to the immobilized binding partner. Contacting the binding partners in the presence and absence of a putative modulator and measuring change in binding will permit identification of potential in vivo binding modulators. The non-immobilized binding partner may be labeled with a radioisotope, a fluorescent marker, or the like. Alternatively, the immobilized binding partner may be bound to a support which includes a compound that can be excited to emit light when in proximity to the binding partner. Association of the binding partner can thereby be quantitated by the degree of light emitted, and modulators identified by the degree to which the level of emitted light is changed.

Additional methods comprehended by the invention include immunological assays including radio-immuno assays, enzyme linked immunosorbent assays, sandwich assays and the like. Co-precipitation methods are also comprehended wherein an antibody immunospecific for one binding partner is utilized in a method in which the other binding partner is detectably labeled. Immunological assays may also include use of labeled antibodies specifically immunoreactive with a complex between the desired binding partners.

Numerous compounds are contemplated as being candidates for testing in methods of the invention. For example, antibody products which are immunoreactive with one binding partner and which modulate binding between the two molecules can be identified by the claimed method. Antibody products contemplated are monoclonal antibodies and fragments thereof, humanized antibodies and/or single chain antibodies. Other molecules which can be screened in the claimed method include peptides, small molecules and libraries composed of either of the same.

Modulators of $\beta_1$ integrin/TRAP2 interaction identified by the methods of the invention are utilized in in vivo or in vitro to affect inflammatory processes involving lymphocytes. In addition, modulating compounds which bind to either the $\beta_1$ integrin or TRAP2 are useful to monitor the level of its binding partner, either in a body fluid or biopsied tissue.

Those of ordinary skill in the art will readily appreciate that numerous variations of the claimed method are encompassed by the invention.

DETAILED DESCRIPTION OF THE INVENTION

The present invention is illustrated by the following examples relating to the isolation of a cDNA clone encoding a protein that interacts with a $\beta_1$ integrin and methods to identify modulators of the interaction. Example 1 describes identification of genes from a B cell library which encode proteins that interact with $\beta_1$ integrins. Example 2 addresses specificity of interaction of the identified protein with $\beta_1$ integrin. Example 3 relates to mapping of sequences required for interaction between B171 and $\beta_1$ integrin. Example 4 addresses applications for modulators identified by the method.

Example 1

Identification of Genes in a B Cell Library Encoding $\beta_1$ Interacting Proteins The two-hybrid system developed in yeast [Durfee, et al., *Genes and Development* 7:555–567 (1993)] was used to screen for products of a human B cell cDNA library which interact with the carboxy-terminus of the cytoplasmic tail of the $\beta_1$ integrin subunit. The yeast two-hybrid screen is based on in vivo reconstitution of the GAL4 transcription factor and subsequent expression of a reporter gene driven by a GAL4 promoter. Briefly, GAL4 DNA-binding and transcription-activating domains are encoded on separate plasmids as portions of fusion proteins. Expression of the fusion proteins and interaction of the expression products results in association of the two GAL4 domains and ultimate expression of the β-galactosidase reporter gene under transcriptional control of the GAL4 promoter.

In the present investigation, a "bait" plasmid (pAS1) was constructed that contained sequences encoding the GAL4-binding domain, a trp$^-$ selection requirement, a hemagglutinin (HA) epitope tag and cytoplasmic amino acid sequences of $\beta_1$ integrin. The cytoplasmic domain for $\beta_1$ was initially isolated from a HeLa cDNA library by standard hybridization techniques using an anti-sense probe beta1.d2 as set out in SEQ ID NO: 1.

AGAAGTAGGTATTCCTTCCTG (SEQ ID NO: 1)

Hybridization was carried out using 22 μl Rapid Hyb solution (Amersham, Arlington Heights, Ill.), 100 μl of 50 μg/ml heparin, and the beta1.d2 probe previously labeled using a Random Primer Labelling kit (Boehringer Mannheim, Indianapolis, Ind.) according to manufacturer's suggested protocol. Hybridization was carried out at 42° C. overnight and a final filter wash was performed in 1X SSC/0.1% SDS at 42° C. The library sequence from a positive clone was subcloned into vector pCDNA1amp, after which the integrin cytoplasmic sequences were amplified by PCR for subsequent subcloning. The $\beta_1$ integrin cytoplasmic domain was amplified by PCR using the primers set out in SEQ ID NOs: 2 and 3.

NHβ₁a5
GGAAGATCTTGAAGCTTTTAATGATAATTC
(SEQ ID NO:2)

NHβ₁a3
GGAAGATCTTCATTTTTCCTCATACTTCGG
(SEQ ID NO:3)

Amplification conditions included an initial incubation at 94° C. for four minutes, followed by thirty cycles of: 94° C. for one minutes, 50° C. for two minutes, and 72° C. for four minutes. The resulting product was sequenced to rule out PCR-derived errors and subcloned into plasmid pAS1. A yeast strain, Y190, was transformed with $\beta_1$/pAS1 by standard methods and grown in selective media (trp⁻) to mid-log phase. Cells were lysed in lysis buffer (containing 100 mM Tris, pH 6.8, 2% SDS, 10% glycerol, 5% BME and 0.1% bromo phenol blue) and the equivalent of 5–6×10⁶ cells of protein was separated on a 12% polyacrylamide gel. Proteins in the gel were then transferred to a PVDF (Millipore) membrane by standard methods. Control lanes on the gel contained lysate from Y190 transformed with pAS1 vector alone (containing no $\beta_1$ integrin-encoding sequences). Western blotting was performed using antibody 12CA5 immunospecific for the HA epitope tag (Boehringer Mannheim, Indianapolis, Ind.), and a goat anti-mouse IgG horse radish peroxidase (HRP) secondary antibody. Results indicated that the fusion protein $\beta_1$ integrin cytoplasmic tail/HA/GAL4 DNA-binding domain was expressed at readily detectable levels.

A "target" vector was constructed with plasmid pACT modified to contain sequences encoding the GAL4 activation domain II fused to a human lymphocyte cDNA library inserted at the XhoI site and a leu⁻ selection requirement. The $\beta_1$/pAS1-transformed Y190 cells were transformed by standard methods with the pACT-lymphocyte library DNA and cells grown under selective conditions (leu⁻/trp⁻/his⁻/ 13-aminothiazole). Only cells in which the GAL4 transcription factor reconstituted as a result of interaction occurred between $\beta_1$ integrin cytoplasmic tail of the "bait" fusion protein and an unknown "target" (B cell library-derived) fusion protein survive. Resulting colonies were tested for β-galactosidase (β-gal) activity and two β-gal positive clones were obtained.

Sequence analysis of the B cell cDNA-derived, pACT inserts identified revealed one sequence which encoded a portion of a known protein. The nucleotide and amino acid sequences for this clone, designated B171, are set out in SEQ ID NOs: 4 and 5, respectively. Comparison of the sequence of clone B171 with DNA and protein databases, via NCBI Blastn and Blastp, on or around Jul. 13, 1995 and again around Nov. 24, 1995, revealed that B171 has high sequence identity to three proteins: TRAP2 (gp or gb/U12596), 26S proteasome subunit p97 (GP or DBJ/D78151), 55.11 binding protein (gp or emb/X86446) which is related to the 26S proteasome subunit p97. B171 is also homologous to a lesser extent to a related protein p67 (gp or gb/U18247). An alignment of the four proteins with each other and with B171 suggests that the four proteins may be the same protein with sequencing errors or artifacts generated during cDNA synthesis explaining the discrepancies between them.

Example 2

Specificity of B171 Interaction With $\beta_1$

The specificity of the interaction between B171 and $\beta_1$-integrin cytoplasmic tail was addressed by transforming B171 into Y190 strains previously transformed with variety of "baits" vectors (encoding any one of $\beta_1$, $\beta_2$, $\beta_7$, $\alpha_L$, and $\alpha_4$-integrin cytoplasmic tails) using standard methods of transformation and selection described above.

Results shown in Table 1 indicate that B171 specifically binds to $\beta_1$ integrins and not to other integrins.

TABLE 1

| $\beta_1$/Integrin Binding Specificity | |
|---|---|
| Bait Integrin | β-Galactosidase Activity |
| $\beta_1$ | + |
| $\beta_2$ | − |
| $\beta_7$ | − |
| $\alpha_L$ | − |
| $\alpha_4$ | − |

Example 3

Localization of B171/$\beta_1$ Binding Sites

In order to determine $\beta_1$ sequences necessary for B171 binding, the cytoplasmic domain sequences of the $\beta_1$ subunit, and various truncation mutants thereof, were cloned and utilized in the two hybrid screen. In this method, only cytoplasmic regions of the integrin subunit were cloned into the bait plasmid. The deletions in the $\beta_1$-integrin cytoplasmic tail were created using standard in vitro mutagenesis schemes using PCR with the primers used to generate each deletion as set out in SEQ ID NO: 6 to 9. Each of the primers used to amplify a deletion mutant was paired with the 5' primer set out in SEQ ID NO: 2.

NHβ1D1
TACGGCACTCTTATACTAAGGATTTTCACCCGT
(SEQ ID NO:6)

NHβ1D2
ATTGACCAGAGTTGTCTAGGCACTCTTATAAAT
(SEQ ID NO:7)

NHβ1D3
TCATTTTCCCTCATACTACGGATTGACCACAGT
(SEQ ID NO:8)

NHβ1D4

-continued
GTCCCATTTGGCATTCTBTTTCTCCTTTTCAAA (SEQ ID NO:9)

The resultant truncation mutants are set out in SEQ ID NOs: 11 to 14, with the wild type sequence of $\beta_1$ shown in SEQ ID NO: 10.

B1
KLLMIIHDRREFAKFEKEKMNAKWDT-
GENPIYKSAVTTVVNPKYEGK
(SEQ ID NO:10)

B1D1
KLMIIHDRREFAKFEKEKMNAKWDTGENP
(SEQ ID NO:11)

B1D2
KLLMIIHDRREFAKEKEKMNAKWDTGENPIYKSA (SEQ ID NO:12)

B1D3
KLLMIIHDRREFAKFEKEKMNAKWDTGENPIYKSAVTTVVNP
(SEQ ID NO:13)

B1D4
KLLMIIHDRREFAKFEKEK
(SEQ ID NO:14)

As shown in Table 2, the only $\beta_1$ integrin mutant to still interact with B171 was B1D3. All the other deletions in the integrin cytoplasmic sequence abolish the interaction.

TABLE 2

| TRAP2 Interaction with $\beta_1$ Deletions | |
|---|---|
| B1 | + |
| B1D1 | − |
| B1D2 | − |
| B1D3 | + |
| B1D4 | − |

Example 4

Applications for Modulating Compounds

Engagement of $\alpha_4\beta_1$ has been shown to induce cytokine gene expression in eosinophils and macrophages [Yurochko, et al., *Proc. Natl. Acad. Sci. (USA)* 89:9034–9038 (1992) and Anwar, et al., *J. Exp. Med.* 177:839–843 (1993)]. Engagement with VCAM-1, matrix proteins, or monoclonal antibodies to $\beta_1$, induces activation of $NF_kB$ [Lofquist, et al., *Mol. Cell. Biol.* 15:1737–1746 (1995)]. $NF_kB$ is associated with rapid production of inflammatory cytokines, chemokines and cell adhesion molecules in many different cell types including macrophages and endothelial cells [see reviews in Siebenlist, *Ann. Rev. Cell Biol.* 10:405–455 (1994) and Baeuerle, *Ann. Rev. Immunol.* 12:141–179 (1994)].

It has also been demonstrated that proteasomes are involved in activation of $NF_kB$, and the invention contemplates that TRAP2 association with the $\beta_1$ integrin subunit also results in $NF_kB$ activation. Inhibitors of this interaction are therefore contemplated to function in vivo as potent anti-inflammatory agents. Development of a high throughput screening (HTS) method which permits rapid analysis of small molecule libraries, peptide libraries and antibodies will provide candidate anti-inflammatory agents for further in vivo analysis. A number of assays disclosed herein, e.g., two hybrid screening, scintillation proximity assay (SPA), various immuno-assays, including enzyme-linked immunosorbent assays (ELISA), etc., while not HST screening methodologies, per se, are amenable to identify binding modulators. SPA and ELISA, in particular, are useful in this respect and can be modified to permit high throughput screening.

Numerous modifications and variations as set forth in the above illustrative examples are expected to occur to those of ordinary skill in the art. Consequently, only such limitations as appear in the appended claim should be placed on the invention.

What is claimed is:

1. A method for identifying a compound that modulates binding between TRAP2/26S proteasome subunit and $\beta_1$ integrin comprising the steps of:

a) contacting TRAP2/26S proteasome subunit or a fragment thereof, with integrin or a fragment thereof;

b) measuring binding between TRAP2/26S proteasome subunit or a fragment thereof, and $\beta_1$ integrin or a fragment;

c) measuring binding between TRAP2/26S proteasome subunit or a fragment thereof, and $\beta_1$ integrin or a fragment in the presence of a test compound; and d) comparing the measurement in step (b) and the measurement in step (c) wherein a decrease in binding in step (c) indicates the test compound in an inhibitor of binding, and an increase in binding in step (c) indicates the test compound is an activator of binding.

* * * * *

UNITED STATES PATENT AND TRADEMARK OFFICE
CERTIFICATE OF CORRECTION

PATENT NO. : 5,693,483
DATED : December 2, 1997
INVENTOR(S) : Staunton *et al.*

It is certified that error appears in the above-identified patent and that said Letters Patent is hereby corrected as shown below:

On the title page:

In Other Publications, under Lofquist *et al.*, replace "etc" with --Regulating I$\kappa$ B$\alpha$--.
Column 2, line 44, replace "integrin" with --integrins in various--.
Column 5, line 58, replace "13-aminothiazole)." with --/3-aminothiazole).
Column 7, line 17, replace under B1D2 "KLLMIIHDRREFAKEKEKMNAKWDTGENPIYKSA" with
    --KLLMIIHDRREFAKFEKEKMNAKWDTGENPIYKSA--.
Column 19, line 35, replace "with integrin" with --with $\beta_1$ integrin--.

Signed and Sealed this

Twenty-third Day of January, 2001

Attest:

Q. TODD DICKINSON

*Attesting Officer*  *Commissioner of Patents and Trademarks*